US011103435B2

(12) United States Patent
Fadel et al.

(10) Patent No.: US 11,103,435 B2
(45) Date of Patent: Aug. 31, 2021

(54) MALODOR REDUCING COMPOSITIONS

(71) Applicant: Givaudan, S.A., Vernier (CH)

(72) Inventors: Addi Fadel, Paris (FR); Philippe Blondeau, Paris (FR); Christian Quellet, Bienne (CH); Anne-Dominique Fortineau, Asnières sur Seine (FR)

(73) Assignee: Givaudan SA, Vernier (CH)

( * ) Notice: Subject to any disclaimer, the term of this patent is extended or adjusted under 35 U.S.C. 154(b) by 803 days.

(21) Appl. No.: 15/517,374

(22) PCT Filed: Jan. 21, 2015

(86) PCT No.: PCT/EP2015/051047
§ 371 (c)(1),
(2) Date: Apr. 6, 2017

(87) PCT Pub. No.: WO2016/058710
PCT Pub. Date: Apr. 21, 2016

(65) Prior Publication Data
US 2017/0290757 A1    Oct. 12, 2017

(30) Foreign Application Priority Data
Oct. 14, 2014    (EP) .................................. 14290307

(51) Int. Cl.
| *A61Q 5/10* | (2006.01) |
| *A61Q 13/00* | (2006.01) |
| *A61K 8/49* | (2006.01) |
| *A61K 8/19* | (2006.01) |
| *A61K 8/33* | (2006.01) |
| *A61K 8/46* | (2006.01) |
| *C11B 9/00* | (2006.01) |

(52) U.S. Cl.
CPC .............. *A61K 8/4926* (2013.01); *A61K 8/19* (2013.01); *A61K 8/33* (2013.01); *A61K 8/46* (2013.01); *A61K 8/4973* (2013.01); *A61Q 5/10* (2013.01); *A61Q 13/00* (2013.01); *C11B 9/003* (2013.01); *C11B 9/0015* (2013.01); *C11B 9/0061* (2013.01); *C11B 9/0084* (2013.01)

(58) Field of Classification Search
None
See application file for complete search history.

(56) References Cited

U.S. PATENT DOCUMENTS

| 8,703,692 B2 | 4/2014 | Kraft et al. |
| 8,784,784 B2 | 7/2014 | Perring et al. |
| 9,125,828 B2 | 9/2015 | Behan et al. |
| 2006/0218730 A1 | 10/2006 | Nagano et al. |
| 2010/0130624 A1 | 5/2010 | Oertling |
| 2011/0104098 A1 | 5/2011 | Bajgrowicz et al. |
| 2012/0305416 A1 | 12/2012 | Miyabe et al. |
| 2012/0309670 A1 | 12/2012 | Kraft et al. |
| 2013/0058881 A1 | 3/2013 | Perring et al. |
| 2013/0129655 A1 | 5/2013 | Goeke et al. |
| 2013/0316940 A1 | 11/2013 | Perring et al. |
| 2013/0336911 A1 | 12/2013 | Behan et al. |

FOREIGN PATENT DOCUMENTS

| JP | 2004-107208 A | 4/2004 |
| WO | WO 2011/098472 A1 | 8/2011 |
| WO | WO 2011/128340 A2 | 10/2011 |
| WO | WO 2012/080235 A1 | 6/2012 |

OTHER PUBLICATIONS

PCT/EP2015/051047—International Search Report, dated Jun. 8, 2015.
PCT/EP2015/051047—International Written Opinion, dated Jun. 8, 2015.
PCT/EP2015/051047—International Preliminary Report on Patentability, dated Apr. 18, 2017.

*Primary Examiner* — Jyothsna A Venkat
(74) *Attorney, Agent, or Firm* — Curatolo Sidoti Co., LPA; Salvatore A. Sidoti; Floyd Trillis, III

(57) ABSTRACT

A malodor reducing composition is provided. The composition includes a perfume mixture including (a) at least one odor-reducing material; and (b) at least one N-heterocycle selected from an aromatic N-heterocyclic moiety and N,S-heterocyclic moiety. The at least one odor-reducing material exhibits an Odor Value (OV) having a common decimal logarithm ($\log_{10}$ OV) of greater than about 5.5.

1 Claim, No Drawings

MALODOR REDUCING COMPOSITIONS

CROSS REFERENCE TO RELATED APPLICATIONS

This application is a national stage application of International Application No. PCT/EP2015/051047, filed 21 Jan. 2015, which claims priority from European Patent Application No. 14290307.9, filed 14 Oct. 2014, which applications are incorporated herein by reference.

FIELD OF THE INVENTION

The present disclosure relates to malodor reducing compositions. More particularly, the present disclosure relates to malodor reducing compositions having certain fragrance ingredients that reduce the sensory perception of a broad range of malodors.

BACKGROUND OF THE INVENTION

Products for the counteraction of malodors are well known in the art. Many commercial, industrial, household, and personal care products are designed to mask malodor in the environment to which they are applied or in which they are used. Products may also generate malodor during and/or upon application or use or may themselves be inherently malodorous due to their constituents and functional raw ingredients.

Malodor inherent to cosmetic, industrial and household formulations is an extensive and ubiquitous problem common to many different applications ranging from household cleaners to personal care products including antiperspirants, deodorants, sunless tanners, hair colorants, shampoos and conditioners, hand and body lotions, hair perming and relaxing agents, and the like.

Some of the most challenging formulations to fragrance are products that contain ammonia, for example, hair colorants. Due to ammonia's physical properties, such as very high vapor pressure, and its very pungent and offensive perceived olfactive profile, ammonia is considered one of the most difficult malodors to cover using targeted malodor covering perfumery.

Covering the perception of ammonia in products, such as hair coloring products, remains a formidable task despite numerous attempts at creating ways and methods to do so. The difficulty to cover ammonia lies in the necessity to cover ammonia physically rather than chemically since the creation of any type of chemical bond between ammonia and another odorant or chemicals in the formulation will result in a less performing, and sometime even unstable product.

Accordingly, there remains a need to provide malodor reducing compositions that reduces the sensory perception of a broad range of malodors, including nitrogen-based, sulfur-based, acidic and aldehydic malodors in consumer products.

SUMMARY OF THE INVENTION

In one embodiment, a malodor reducing composition includes a perfume mixture including (a) at least one odor-reducing material; and (b) at least one N-heterocycle selected from an aromatic N-heterocyclic moiety and N,S-heterocyclic moiety. The at least one odor-reducing material exhibits an Odor Value (OV) having a common logarithm ($\log_{10}$ OV) of greater than about 5.5.

In another embodiment, a consumer product includes a perfume mixture and a nitrogen based component. The perfume mixture includes (i) at least one odor-reducing material; and (ii) at least one N-heterocycle selected from an aromatic N-heterocyclic moiety and N,S-heterocyclic moiety. The nitrogen based component includes a nitrogen based component selected from the group consisting of ammonia, substituted amine, and mixtures thereof. The at least one odor-reducing material exhibits an Odor Value (OV) having a common logarithm ($\log_{10}$ OV) of greater than about 5.5.

In yet another embodiment, a hair colorant composition includes a perfume mixture and a nitrogen based component. The perfume mixture includes (i) at least one odor-reducing material; and (ii) at least one N-heterocycle selected from an aromatic N-heterocyclic moiety and N,S-heterocyclic moiety. The nitrogen based component includes a nitrogen based component selected from the group consisting of ammonia, substituted amine, and mixtures thereof. The at least one odor-reducing material exhibits an Odor Value (OV) having a common logarithm ($\log_{10}$ OV) of greater than about 5.5.; an Odor Detection Threshold ($ODT_i$) of from about 0.001 to about 160 (ng/L); and a Standard Equilibrium Headspace Concentration ($HS_i^o$) of from about 0.1 to about 100,000 (µg/L).

These and other features, aspects and advantages of specific embodiments will become evident to those skilled in the art from a reading of the present disclosure.

DETAILED DESCRIPTION OF THE INVENTION

The following text sets forth a broad description of numerous different embodiments of the present disclosure. The description is to be construed as exemplary only and does not describe every possible embodiment since describing every possible embodiment would be impractical, if not impossible. It will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

The present disclosure relates to malodor reducing compositions and methods thereof. Malodor reducing compositions according to the present disclosure include perfume mixtures that reduce the sensory perception of a broad range of malodors, including for example, nitrogen-based, sulfur-based, acidic and aldehydic malodors.

"Malodor" refers to compounds generally offensive or unpleasant to most people, such as the odors associated with nitrogen-based, sulfur-based, acidic and aldehydic malodors.

"Odor Value" of a perfume ingredient is defined as the ratio of the Standard Equilibrium Headspace Concentration ($HS_i^o$), expressed in microgram/l/the Odor Detection Threshold ($ODT_i$), also expressed in microgram/l.

The term "$\log_{10}$ OV" refers to the common (or decimal) logarithm of Odor Value defined above.

"Odor Detection Threshold" ($ODT_i$) refers to the average concentration above which an odorant (i) can be perceived by a panelist and can be measured using an olfactometer.

"Standard Equilibrium Headspace Concentration" refers to the concentration of the ingredient in equilibrium with the condensed form, that is, solid or liquid form of this ingredient at a temperature of 20° C. and under a pressure of 1 atmosphere. It can be measured by using any of the known quantitative headspace analysis techniques, see for example Mueller and Lamparsky in Perfumes: Art, Science and Technology, Chapter 6 "The Measurement of Odors" at pages 176-179 (Elsevier 1991).

A. Perfume Mixture

According to the present disclosure, malodor reducing compositions include a perfume mixture including at least one odor-reducing material; and at least one N-heterocycle. The malodor reducing composition may also other optional ingredients for particular applications. An odor-reducing material and a N-heterocycle are selected based upon their ability to mask malodor caused by the presence of nitrogen-based (for example, ammonia, methylamine, ethylamine, dimethyamine, indole, skatole, and cadaverine), sulfur-based (for example, hydrogen sulfide, methylmercaptan, ethylmercaptan, dimethylsulfide, diethylsulfide, and dimethyldisulfide), acidic malodors (for example, acetic, butyric and valeric) and aldehydic malodors (for example, formaldehyde, acetaldehyde, butyraldehyde and isovaleraldehyde).

This ability is determined by a number of factors, including, for example, the common decimal logarithm of Odor Value ($\log_{10}$ OV), and is used to formulate malodor reducing compositions to mask malodor. In another embodiment, factors may also include odor threshold (ng/L) and vapor pressure (µg/L) in order to determine the perfume ingredients ability to cover malodor.

The malodor reducing composition of the present disclosure may be used in a wide variety of applications and are not restricted to any particular physical mode or product form. According to the present disclosure, one example of a consumer product includes hair coloring/treatment products. Although, the embodiments described herein in detail are directed towards hair coloring/treatment products, the disclosure is applicable to various cosmetic and personal care products, such as for example, fabric and air freshening sprays and body deodorants, laundry detergents and additives, room fresheners or room deodorants, household cleansers, toilet bowl cleaners, dish detergents, body washes, shampoos, conditioners and the like.

Malodor reducing compositions may also be used in a number of malodorous containing environments or products. For example, and not as a limitation to the present disclosure, environments such as landfills, cat litter, chicken coops, water treatment plants and ponds, garbage, dog kennels, rendering plants, food processing plants, wool plants, fish canneries, sewers, septic tanks, paper mills and rest rooms, and products for bathroom care, room freshening, air freshening, pet care, adult incontinence, household cleaning, hair treatment, hard surface cleaning, and the like. However, for convenience, the discussion below will focus on ammonia and substituted amine environments, for example, hair coloring/treatment products.

Without being limited by theory, it is believed that malodorous amine containing environments the perfumery mixture of the present disclosure provides the effect of substantially decreasing ammonia/substituted amine stimulation of the trigeminal (fifth cranial) nerve. The term "substantially decreases trigeminal stimulation," as used herein, means that, at a minimum, the stinging or burning sensation in the nose caused by ammonia/amine based malodors is perceived at an equal or lesser level than the odor of the fragrance component of the composition. It is believed that when the trigeminal nerve is stimulated by the high-ammonia/amine compositions, the burning or stinging sensation predominates over any perfumery odors which stimulate olfactory senses, e.g., the sense of smell.

1. Odor-Reducing Materials

In accordance with one embodiment, the malodor reducing composition according to the present disclosure may include at least one odor-reducing material to mitigate the effects of malodors. Suitable odor-reducing materials may have an Odor Value (OV) having a common decimal logarithm ($\log_{10}$ OV) of greater than about 5.5; in another embodiment $\log_{10}$ OV is greater than about 6.0; in another embodiment $\log_{10}$ OV is greater than about 6.4; and in yet another embodiment $\log_{10}$ OV is greater than about 7.0.

The odor-reducing materials according to the present disclosure may also be defined by their Standard Equilibrium Headspace Concentration ($HS_i^0$) and Odor Detection Threshold ($ODT_i$). In one embodiment, suitable odor-reducing materials may have a $HS_i^0$ in the range of from about 0.10 to about 100,000 µg/L, or any individual number within the range. In another embodiment, the $HS_i^0$ headspace concentration may be from about 1.0 to about 10,000 µg/L; and in yet another embodiment the $HS_i^0$ headspace concentration may be from about 10 to about 5,000 µg/L.

With respect to Odor Detection Threshold, suitable odor-reducing materials may have an $ODT_i$ in the range of from about 0.001 to about 160 ng/L, or any individual number within the range. In another embodiment, the $ODT_i$ may be from about 0.01 to about 100 ng/L; and in yet another embodiment the $ODT_i$ may be from about 0.05 to about 10 ng/L.

Suitable odor-reducing materials according to the present disclosure include saturated alkyl aldehydes including, but not limited to, ALDEHYDE C 12 MNA (2-methylundecanal); ALDEHYDE C 8 OCTYLIC (octanal); ALDEHYDE C 9 (nonanal); ALDEHYDE C 6 HEXYLIC (hexanal); CALYPSONE (6-methoxy-2,6-dimethyloctanal); and ALDEHYDE C 7 HEPTYLIC (heptanal). In one embodiment, the saturated alkyl aldehydes are selected from the group consisting of ALDEHYDE C 12 MNA and CALYPSONE.

In another embodiment, suitable odor-reducing materials include unsaturated alkyl aldehydes including, but not limited to, DECEN-1-AL, CIS-4 ((Z)-dec-4-enal); DECENAL-4-TRANS ((E)-dec-4-enal); DECENAL-9 (9-decenal), MELONAL (2,6-dimethylhept-5-enal); CYCLAL C (2,4-dimethylcyclohex-3-enecarbaldehyde); NONADIENAL ((2E,6Z)-nona-2,6-dienal); PINOACETALDEHYDE (3-(6,6-dimethylbicyclo[3.1.1]hept-2-en-2-yl)propanal); SHISOLIA (4-vinylcyclohex-1-enecarbaldehyde); and MACEAL (bicyclo[2.2.2]oct-5-ene-2-carboxaldehyde). In one embodiment, the unsaturated alkyl aldehydes are selected from the group consisting of MELONAL, CYCLAL C, SHISOLIA and MACEAL.

In another embodiment, suitable odor-reducing materials include aromatic aldehydes including, but not limited to, AUBEPINE PARA CRESOL (4-methoxybenzaldehyde), FLORHYDRAL (3-(3-isopropylphenyl)butanal); PHENYL PROPIONIC ALDEHYDE (3-phenylpropanal); and TOLYL ALDEHYDE PARA (4-methylbenzaldehyde).

In another embodiment, suitable odor-reducing materials include glycolates including, but not limited to, ALLYL AMYL GLYCOLATE (allyl 2-(isopentyloxy)acetate).

In another embodiment, suitable odor-reducing materials include alcohols, including, but not limited to, AMYL VINYL CARBINOL (oct-1-en-3-ol); LINALOOL (3,7-dimethylocta-1,6-dien-3-ol); NONADIENOL-2,6 ((2E,6Z)- nona-2,6-dien-1-ol); NONENOL-6-CIS ((Z)-non-6-en-1-ol); POLYSANTOL ((E)-3,3-dimethyl-5-(2,2,3-trimethyl-3-cyclopenten-1-yl)-4-penten-2-ol); and DIMETOL (2,6-dimethylheptan-2-ol); HEXENOL-3 CIS (cis-hex-3-en-1-ol). In one embodiment, the alcohols are selected from the group consisting of LINALOOL, NONADIENOL-2,6, NONENOL-6-CIS, POLYSANTOL, DIMETOL, and HEXENOL-3 CIS.

In another embodiment, suitable odor-reducing materials include sulfur-containing perfumery ingredients, including, but not limited to, ANJERUK (1-phenylethanethiol); CORPS PAMPLEMOUSSE ((4S)-4,7,7-trimethyl-6-thiabicyclo[3.2.1]octane); PARA MERCAPTO MENTHENE (2-(4-methylcyclohex-3-en-1-yl)propane-2-thiol); and THIOGERANIOL ((E)-3,7-dimethylocta-2,6-diene-1-thiol).

In another embodiment, suitable odor-reducing materials include benzodioxepines including, but not limited to, CALONE (7-methyl-2H-benzo[b][1,4]dioxepin-3(4H)-one); and AZURONE (7-isopentyl-2H-benzo[b][1,4]dioxepin-3 (4H)-one).

In another embodiment, suitable odor-reducing materials include ketones including, but not limited to, CARVONE LAEVO (2-methyl-5-(prop-1-en-2-yl)cyclohex-2-enone); DAMASCENONE ((E)-1-(2,6,6-trimethylcyclohexa-1,3-dien-1-yl)but-2-en-1-one); DAMASCONE ALPHA ((E)-1-(2,6,6-trimethylcyclohex-2-en-1-yl)but-2-en-1-one); DAMASCONE BETA ((E)-1-(2,6,6-trimethylcyclohex-1-en-1-yl)but-2-en-1-one); DAMASCONE DELTA ((E)-1-(2,6,6-trimethylcyclohex-3-en-1-yl)but-2-en-1-one); FILBERTONE ((E)-5-methylhept-2-en-4-one); GALBANONE (1-(3,3-dimethylcyclohex-1-en-1-yl)pent-4-en-1-one); IRISANTHEME ((E)-3-methyl-4-(2,6,6-trimethylcyclohex-2-en-1-yl)but-3-en-2-one); NEROLIONE (1-(3-methylbenzofuran-2-yl)ethanone); PHARAONE (2-cyclohexylhepta-1,6-dien-3-one); POMAROSE ((2E,5E)-5,6,7-trimethylocta-2,5-dien-4-one); IRISONE ALPHA (E)-4-(2,6,6-trimethylcyclohex-2-en-1-yl)but-3-en-2-one; IRISONE BETA (E)-4-(2,6,6-trimethylcyclohex-1-en-1-yl)but-3-en-2-one; and DIHYDRO JASMONE (3-methyl-2-pentylcyclopent-2-enone).

In another embodiment, suitable odor-reducing materials include cyclic oxides, furans, pyrans and their partially or fully hydrogenated derivatives including, but not limited to, CASSYRANE (5-tert-butyl-2-methyl-5-propyl-2H-furan); ROSYRANE (4-methylene-2-phenyltetrahydro-2H-pyran); PELARGENE (2-methyl-4-methylene-6-phenyltetrahydro-2H-pyran); RHUBAFURAN (2,4-dimethyl-4-phenyltetrahydrofuran); ROSE OXIDE (4-methyl-2-(2-methylprop-1-en-1-yl)tetrahydro-2H-pyran); and EUCALYPTOL ((1s,4s)-1,3,3-trimethyl-2-oxabicyclo[2.2.2]octane).

In another embodiment, suitable odor-reducing materials include phenols including, but not limited to, CREOSOL (2-methoxy-4-methylphenol); DIHYDRO EUGENOL (2-methoxy-4-propylphenol); GUAIACOL (2-methoxyphenol); ULTRAVANIL (2-ethoxy-4-methylphenol); and EUGENOL (4-allyl-2-methoxyphenol).

In another embodiment, suitable odor-reducing materials include phenol esters including, but not limited to, CRESYL ACETATE PARA (p-tolyl acetate); CRESYL ISOBUTYRATE PARA (p-tolyl isobutyrate); and PANDANOL (2-methoxyethyl)benzene);

In another embodiment, suitable odor-reducing materials include nitriles including, but not limited to, CUMIN NITRILE (4-isopropylbenzonitrile); and VIOLET NITRILE ((2E,6Z)-nona-2,6-dienenitrile).

In another embodiment, suitable odor-reducing materials include aromatic ethers, including, but not limited to, DIHYDRO ANETHOLE (1-methoxy-4-propylbenzene); and TOSCANOL (1-(cyclopropylmethyl)-4-methoxybenzene).

In another embodiment, suitable odor-reducing materials include esters including, but not limited to, ETHYL SAFRANATE (ethyl 2,6,6-trimethylcyclohexa-1,3-diene-1-carboxylate); FOLIONE (methyl oct-2-ynoate); HEXENYL ACETATE, CIS-3 (cis-hex-3-enyl acetate); METHYL PHENYL ACETATE (methyl 2-phenylacetate); ETHYL 2-METHYL BUTYRATE (ethyl 2-methylbutanoate); ETHYL ISOBUTYRATE (ethyl 2-methylpropanoate); ETHYL ISOVALERATE (ethyl 3-methylbutanoate); ETHYL PROPIONATE (ethyl propanoate); and PRENYL ACETATE (3-methylbut-2-en-1-yl acetate).

In another embodiment, suitable odor-reducing materials include lactones including, but not limited to, KOUMALACTONE (3,6-dimethyl-3a,4,5,6,7,7a-hexahydro-3H-benzofuran-2-one); and PRUNOLIDE (5-pentyldihydrofuran-2(3H)-one).

In another embodiment, suitable odor-reducing materials include anthranilates including, but not limited to, METHYL ANTHRANILATE (methyl 2-aminobenzoate).

In another embodiment, suitable odor-reducing materials include carboxylic acids including, but not limited to, PHENYL ACETIC ACID PURE (2-phenylacetic acid).

In another embodiment, suitable odor-reducing materials include terpenes and hydrocarbons including, but not limited to, UNDECATRIENE ((3E,5Z)-undeca-1,3,5-triene); and MYRCENE (7-methyl-3-methyleneocta-1,6-diene).

Hydrophobicity of the above odor-reducing material can be measured using log P value, a physico-chemical property. The octanol/water partition coefficient (P) of an odor-reducing material is the ratio between its equilibrium concentrations in octanol and in water. The log P values can also be very conveniently calculated using the fragment approach of Hansch and Leo and given as clog P. See A. Leo, Comprehensive Medicinal Chemistry, Vol 4, C. Hansch et al. p 295, Pergamon press, 1990 and given as clog P. According to the present disclosure, the at least one odor-reducing material may have a clog P of about 4 or less; in another embodiment, the at least one odor-reducing material may have a clog P of about 3 or less; and in yet another embodiment, the at least one odor-reducing material may have a clog P of about 2.5 or less.

The perfume mixture may comprise from about 0.0001% to about 99%, or any individual number within the range, by weight of the perfume mixture of an odor-reducing material. In another embodiment, the perfume mixture may comprise at least about 0.001%, by weight of the perfume mixture of an odor-reducing material; in another embodiment, at least about 1.0%, by weight of the perfume mixture of an odor-reducing material; and in yet another embodiment, at least about 5.0%, by weight of the perfume mixture of an odor-reducing material.

2. N-Heterocycles

In accordance with one embodiment, the malodor reducing composition according to the present disclosure may also include at least one N-heterocycle to mitigate the effects of malodors. It has been found that certain N-heterocycles have a positive impact on ammonia and amine malodor coverage in certain applications.

In one embodiment, N-heterocycles include at least one perfume ingredient having one aromatic N-heterocyclic moiety or one N,S-heterocyclic moiety. In another embodiment, suitable N-heterocycles include, but are not limited to, BIGARYL (8-(sec-butyl)-5,6,7,8-tetrahydroquinoline), ETHYL DIMETHYL PYRAZINE (5-ethyl-2,3-dimethylpyrazine), ISOBUTYL METHOXY PYRAZINE (2-isobutyl-3-methoxypyrazine), METHOXY METHYL PYRAZINE (2-methoxy-3-methylpyrazine), METHYL ISOPROPYL THIAZOL (2-ethyl-4-methyl-1,3-thiazole), VETHYMINE (2,4-diethoxy-5-methylpyrimidineZINARINE (2-(2,4-dimethylcyclohexyl)pyridine), 8-(pentan-2-yl)-5,6,7,8-tetrahydroquinoline, 8-(pentan-3-yl)-5,6,7,8-tetrahydroquinoline,7-sec-butyl-6,7-dihydro-5H-cyclopenta[b]pyridine, 7-(pentan-2-yl)-6,7-dihydro-5H-cyclopenta[b]pyridine, 7-(pentan-3-yl)-6,7-dihydro-5H-cyclopenta[b]pyridine,7-(3-methylbut-2-enyl)-6,7-dihydro-5H-cyclopenta[b]pyridine, BUTYL QUINOLINE SECONDARY (6-(sec-butyl)quinoline), ISOBUTYL QUINOLINE (2-isobutylquinoline), ISOPROPYL QUINOLINE (6-isopropylquinoline), METHYL QUINOLINE PARA (6-methylquinoline), PYRALONE (6-(sec-butyl)quinoline), CORPS RACINE (2-(3-phenylpropyl)pyridine), CORYLONE PYRAZINE (5-methyl-6,7-dihydro-5H-cyclopenta[b]pyrazine), HYDROXY ETHYL METHYL THIAZOL (4-ethyl-5-methylthiazol-2-ol), ISOHEXYL METHOXY PYRAZINE (2-methoxy-3-(4-methylpentyl)pyrazine), iso-quinoline, 5-methyl-quinoxaline.

In one embodiment, suitable N-heterocycles have an Odor Value (OV) having a common, decimal logarithm ($\log_{10}$ OV) of greater than about 5.5.

The perfume mixture may comprise from about 0.0001% to about 99%, in another embodiment from about 0.0001% to about 35%, in another embodiment from about 0.001% to about 10%, in yet another embodiment from about 0.01% to about 5%, or any individual number within the range, by weight of the perfume mixture of a N-heterocycle. In another embodiment, the perfume mixture may comprise at least about 0.0001%, by weight of the perfume mixture of a N-heterocycle; in another embodiment, at least about 0.001%, by weight of the perfume mixture of a N-heterocycle; and in yet another embodiment, at least about 0.01%, by weight of the perfume mixture of a N-heterocycle.

Without wishing to be bound by theory, it is believed that when a N-heterocycle is present with an odor-reducing material having a $\log_{10}$ OV greater than about 5.5, the N-heterocycle may increase the efficacy of the perfume mixture on malodors caused by the presence of ammonia and substituted amines in comparison to the malodor efficacy of the odor-reducing material on its own.

3. Optional Ingredients

The malodor reducing compositions may, optionally, include additional ingredients which include, but are not limited to, thickeners, solvents, enzymes, stabilizers, surfactants, chelants and oxidizing agents depending on the method of use. In one embodiment, for example, hair coloring compositions may include viscosity/gel strength modifiers, oils and fats, waxes, hydrocarbons, polyhydric alcohols, amides, silicone derivatives, cationic surfactants, anionic surfactants, amphoteric surfactants, nonionic surfactants, nonionic high-molecular substances, cationic high-molecular substances, anionic high-molecular substances, amphoteric high-molecular substances, protein derivatives and amino acids, preservatives, chelating agents, stabilizers, oxidation inhibitors, plant extracts, crude drug extracts, vitamins, color additives, fragrances, pigments, ultraviolet absorbers and the like as additives.

EXAMPLES

The following examples are given solely for the purpose of illustration and are not to be construed as limitations of the present invention, as many variations of the invention are possible without departing from the spirit and scope of the present disclosure. Examples 3 and 4 are perfume mixtures suitable for malodor reducing compositions according to the present disclosure. Examples 1 and 2 are comparatives.

The first malodor reducing composition includes a perfume mixture that is a woody fragrance (Example 1). Example 1 includes low odor value materials (($\log_{10}$ OV) of less than 5.5). Example 1 does not contain a N-heterocycle.

Example 1

| Woody Fragrance | | | |
|---|---|---|---|
| Perfume Material | CAS Number | Parts | $\text{Log}_{10}\text{OV}$ |
| ISO E SUPER | 54464-57-2 | 500 | 4.5 |
| DIHYDRO MYRCENOL | 18479-58-8 | 384.5 | 5.4 |
| NIRVANOLIDE | 329925-33-9 | 50 | 4.3 |
| SUPER MUGUET | 26330-65-4 | 30 | 4.0 |
| EBANOL | 67801-20-1 | 20 | 5.3 |
| JASMATONE | 13074-65-2 | 10 | 4.8 |
| PASHMINOL | 1181244-95-0 | 5 | 3.2 |
| METHYL DIANTILIS | 5595-79-9 | 0.5 | 3.9 |

The second malodor reducing composition includes a perfume mixture that is a green fragrance (Example 2). Example 2 includes high odor value materials (($\log_{10}$ OV) of greater than about 5.5). Example 2 also does not contain a N-heterocycle.

Example 2

| Green Fragrance | | | |
|---|---|---|---|
| Perfume Material | CAS Number | Parts | $\text{Log}_{10}\text{OV}$ |
| LINALOL SYNT | 78-70-6 | 310 | 5.8 |
| DIMETOL | 13254-34-7 | 300 | 5.5 |
| HEXENOL-3-CIS | 928-96-1 | 70 | 5.6 |
| ALLYL AMLY GLYCOLATE | 67634-00-8 | 50 | 5.8 |
| IRISONE ALPHA | 8013-90-9 | 50 | 5.1 |
| ALD C12 MNA PUR | 110-41-8 | 50 | 7.0 |
| CYCLAL C | 68039-49-6 | 50 | 5.9 |
| CARVONE LAEVO | 6485-40-1 | 25 | 5.8 |
| MELONAL | 106-72-9 | 20 | 6.6 |
| PHARAONE 10%/DPG | | 20 | 6.2 |
| NEROLIONE | 23911-56-0 | 10 | 7.3 |
| GALBANONE PURE | 56973-85-4 | 10 | 6.6 |
| RHUBAFURAN | 82461-14-1 | 10 | 5.9 |
| ROSE OXIDE CO | 16409-43-1 | 7 | 7.4 |
| UNDECATRIENE | 16356-11-9 | 5 | 6.7 |
| TOSCANOL | 16510-27-3 | 5 | 5.7 |
| CALONE 1951 | 28940-11-6 | 5 | 6.0 |
| NONENOL-6-CIS | 35854-86-5 | 2 | 5.8 |
| NONADIENOL-2,6 | 7786-44-9 | 1 | 7.1 |

The third malodor reducing composition includes a perfume mixture that is a green fragrance (Example 3). Example 3 includes high odor value materials (($\log_{10}$ OV) of greater than about 5.5). Example 3 also contains at least one N-heterocycle (BIGARYL AND ZINARINE).

Example 3

Green Fragrance

| Perfume Material | CAS Number | Parts | Log₁₀OV |
|---|---|---|---|
| LINALOL SYNT | 78-70-6 | 300 | 5.8 |
| DIMETOL | 13254-34-7 | 300 | 5.5 |
| HEXENOL-3-CIS | 928-96-1 | 70 | 5.6 |
| ALLYL AMLY GLYCOLATE | 67634-00-8 | 50 | 5.8 |
| IRISONE ALPHA | 8013-90-9 | 50 | 5.1 |
| ALD C12 MNA PUR | 110-41-8 | 50 | 7.0 |
| CYCLAL C | 68039-49-6 | 50 | 5.9 |
| CARVONE LAEVO | 6485-40-1 | 25 | 5.8 |
| MELONAL | 106-72-9 | 20 | 6.6 |
| PHARAONE 10%/DPG | | 20 | 6.2 |
| NEROLIONE | 23911-56-0 | 10 | 7.3 |
| GALBANONE PURE | 56973-85-4 | 10 | 6.6 |
| RHUBAFURAN | 82461-14-1 | 10 | 5.9 |
| ROSE OXIDE CO | 16409-43-1 | 7 | 7.4 |
| UNDECATRIENE | 16356-11-9 | 5 | 6.7 |
| TOSCANOL | 16510-27-3 | 5 | 5.7 |
| CALONE 1951 | 28940-11-6 | 5 | 6.0 |

-continued

Green Fragrance

| Perfume Material | CAS Number | Parts | Log₁₀OV |
|---|---|---|---|
| BIGARYL | 1401913-94-7 | 5 | 6.6 |
| ZINARINE | 885702-72-7 | 5 | 5.4 |

Perfume composition Examples 1 through 3 are assessed by a panel of a suitable number, for example, 6 expert panelists who have been trained to rate the Ammonia Odor Reduction and assign a score for Ammonia Odor Reduciton, based on the scale in Table 1.

TABLE 1

Expert Sensory Ammonia Discomfort (Intensity)

| Score | Description Corresponding to Score |
|---|---|
| 0 | No Ammonia Discomfort |
| 1 | Very little Ammonia Discomfort |
| 2 | Little Ammonia Discomfort |
| 3 | Moderate Ammonia Discomfort |
| 4 | Strong Ammonia Discomfort |
| 5 | Very Strong Ammonia Discomfort |

Test Methods

The test methods and apparatus described below may be useful in testing embodiments of the present disclosure.

Formulations containing Example 1-3 were put at 0.7% in an in-house permanent hair colorant as described below and evaluated.

The permanent hair colorant is as follows:

| PHASE A | | | |
|---|---|---|---|
| DEIONISED WATER | | Deionised water | 57.85 |
| CARBOPOL U 10 | NOVEON | Carbomer | 0.20 |
| PROPYLENE GLYCOL | PROD'HYG | Propylene glycol | 3.00 |
| COVASTYLE MBS | LCW | Sodium metabisulfite | 0.45 |
| LANETTE E | COGNIS | Sodium cetearyl sulfate | 1.00 |
| PHASE B | | | |
| LANETTE O | COGNIS | Cetearyl alcohol | 5.00 |
| CUTINA AGS | COGNIS | Glycol distearate | 1.00 |
| SYMPATENS ACS/250 | KOLB | Ceteareth-25 | 1.60 |
| SYMPATENS ALM/040 | KOLB | Laureth-4 | 2.90 |
| SYMPATENS ALM/230 | KOLB | Laureth-23 | 1.00 |
| PRIFRAC 2960 | UNIQEMA | Palmitic Acid | 5.00 |
| PHASE C | | | |
| COVASILIC 15 | LCW | Silica dimethyl silylate | 1.00 |
| PHASE D | | | |
| TRIETHANOLAMINE | BASF | Triethanolamine | qsp pH = 8 (4.5%) |
| PHASE E | | | |
| EUMULGIN BL 309 | COGNIS | Deceth-3 | 7.50 |
| AMMONIAC (20%) | PROLABO | Ammoniac | 12.00 |
| PHASE F | | | |
| PERFUME | GIVAUDAN | Perfume | 0.50 |

PROCESS:
Heat Phase A and B separately at 80° C. under stirring.
Add Phase C to Phase B under stirring.
Add Phase A to Phase B under stirring.
Let cool down at 40° C. adjust pH with Phase D.
Then, add raw materials of Phase E one by one.

The formulations were first assessed based in 40 ml glass jars. The jars were left open for 30 seconds to equilibrate before first assessment. The second assessment was done upon mixing the permanent hair colorant formulation with equal volume of hydrogen peroxide solution 20 Volume. The panelists recorded the Ammonia Discomfort perceived directly upon assessing the jar or a bowl containing the hair colorant formulation alone and later the mixture of hydrogen peroxide and hair colorant formulations.

The results are documented below (Table 2) for two different formulations containing respectively 6% and 14% ammonium hydroxide. The results are recorded as an average of the panelist's scores.

TABLE 2

|  | Ammonia Discomfort (hair colorant only) | Ammonia Discomfort (plus hydrogen peroxide) |
|---|---|---|
| 6% Ammonia | | |
| Woody Fragrance (Example 1) | 3 | 2.5 |
| Green Fragrance (Example 2) | 2.4 | 2.2 |
| Green Fragrance (Example 3) | 1.7 | 1.5 |
| 14% Ammonia | | |
| Woody Fragrance (Example 1) | 3.5 | 3.5 |
| Green Fragrance (Example 2) | 2.7 | 2.5 |
| Green Fragrance (Example 3) | 2.2 | 2.1 |

A fourth malodor reducing composition includes a perfume mixture that is a petitgrain type fragrance (Example 4). Example 4 includes high odor value materials (($\log_{10}$ OV) of greater than about 5.5). Example 4 also contains at least one N-heterocycle (BIGARYL).

Example 4

| Perfume Material | CAS Number | Parts | $\log_{10}$OV |
|---|---|---|---|
| EUCALYPTOL COSMOS | 470-82-6 | 705 | 7.0 |
| NEROLIONE | 23911-56-0 | 100 | 7.3 |
| SAFRANATE ETHYLE | 35044-59-8 | 100 | 6.2 |
| ALDEHYDE C 12 MNA PURE | 110-41-8 | 50 | 7.0 |
| MELONAL | 106-72-9 | 20 | 6.6 |
| RHUBAFURAN | 82461-14-1 | 10 | 5.9 |
| UNDECATRIENE | 16356-11-9 | 5 | 6.7 |
| BIGARYL | 1401913-94-7 | 10 | 6.6 |

A formulation containing Example 4 was put at 0.7% in the above described hair colorant provided by formulation with 14% ammonium hydroxide and assessed by a panel based on the scale in Table 1. The formulation was first assessed based in a 40 ml glass jar. The jar was left open for 30 seconds to equilibrate before first assessment. The second assessment was done upon mixing the permanent hair colorant formulation with equal volume of hydrogen peroxide solution. The Ammonia Discomfort was recorded as 2.0 by the panel after consensus.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An ammonia based malodor reducing hair colorant composition comprising:
    a perfume mixture including (a) at least one odor-reducing material; and (b) at least one N-heterocycle, wherein the perfume mixture is present in an amount from about 0.0001% to about 99%, by weight of the malodor reducing hair colorant composition;
    wherein the at least one odor-reducing material exhibits an Odor Value (OV) having a common decimal logarithm ($\log_{10}$ OV) of greater than about 5.5, an Odor Detection Threshold ($ODT_i$) of from about 0.001 to about 160 (µg/L) and a Standard Equilibrium Headspace Concentration ($HS_i^0$) of from about 0.1 to about 100,000 (µg/L),
    wherein the at least one odor-reducing material is selected from the group consisting of saturated alkyl aldehydes, unsaturated alkyl aldehydes, alcohols, ketones, benzodioxepines, sulfur-containing perfumery ingredients and esters;
    wherein said saturated alkyl aldehydes are selected from the group consisting of 2-methylundecanal and 6-methoxy-2,6-dimethyloctanal;
    wherein said unsaturated alkyl aldehydes are selected from the group consisting of 2,6-dimethylhept-5-enal, 2,4-dimethylcyclohex-3-enecarbaldehyde, 4-vinylcyclohex-1-enecarbaldehyde, and bicyclo[2.2.2]oct-5-ene-2-carboxaldehyde;
    wherein said alcohols are selected from the group consisting of 3,7-dimethylocta-1,6-dien-3-ol, (2E,6Z)-nona-2,6-dien-1-ol, (Z)-non-6-en-1-ol, (E)-3,3-dimethyl-5-(2,2,3-trimethyl-3-cyclopenten-1-yl)-4-penten-2-ol, 2,6-dimethyl heptan-2-ol, and cis-hex-3-en-1-ol;
    wherein said benzodioxepines are selected from the group consisting of 7-methyl-2H-benzo[b][1,4]dioxepin-3(4H)-one and 7-isopentyl-2H-benzo[b][1,4]dioxepin-3(4H)-one;
    wherein said ketones are selected from the group consisting of 2-methyl-5-(prop-1-en-2-yl)cyclohex-2-enone, 1-(3,3-dimethylcyclohex-1-en-1-yl)pent-4-en-1-one, (E)-3-methyl-4-(2,6,6-trimethylcyclohex-2-en-1-yl)but-3-en-2-one, 1-(3-methylbenzofuran-2-yl)ethanone, 2-cyclohexylhepta-1,6-dien-3-one, (E) 4-(2,6,6-trimethylcyclohex-2-en-1-yl)but-3-en-2-one, (E)-4-(2,6,6-trimethylcyclohex-1-en-1-yl)but-3-en-2-one, and 3-methyl-2-pentylcyclopent-2-enone;
    wherein said esters are selected from the group consisting of Hexenyl acetate, cis-3, Hexenyl propionate, and cis-3 Methyl phenyl acetate;
    wherein the sulfur-containing perfumery ingredient is 1-phenylethanetriol; and
    wherein the at least one N-heterocycle is selected from the group consisting of 8-(sec-Butyl)-5,6,7,8-tetrahydroquinoline and 2-(2,4-dimethylcyclohexyl)pyridine.

* * * * *